United States Patent [19]

Sureau et al.

[11] 4,027,657

[45] June 7, 1977

[54] FOETAL HEART RATE APPARATUS AND METHOD IN WHICH AVERAGE FOETAL HEART RATE DURING NON-DECELERATION PERIODS IS COMPARED WITH THE AVERAGE FOETAL HEART RATE OVER A FEWER NUMBER OF PERIODS

[75] Inventors: Claude Sureau; Michel Tournaire, both of Paris; Jean-René Zorn, Bourg-la-Reine; Gilbert Sturbois, Paris; Jacques Chavinié, Saint-Maur; Roger Le Houezec, Villejuif; André Ripoche, Vitry-sur-Seine, all of France

[73] Assignee: Agence Nationale de Valorisation de la Recherche (ANVAR), Neuily sur Seine, France

[22] Filed: Apr. 15, 1975

[21] Appl. No.: 568,160

[30] Foreign Application Priority Data

Apr. 17, 1974   France ................................ 74.13270

[52] U.S. Cl. ....................... 128/2.06 F; 128/2.06 A
[51] Int. Cl.² ............................................ A61B 5/04

[58] Field of Search ................. 128/2.05 T, 2.06 A, 128/2.06 F

[56] References Cited

UNITED STATES PATENTS

| 3,575,162 | 4/1971 | Gaarder | 128/2.06 A |
| 3,599,628 | 8/1971 | Abbenante et al. | 128/2.06 F |
| 3,780,725 | 12/1973 | Goldberg | 128/2.05 T |
| 3,878,833 | 4/1975 | Arneson et al. | 128/2.06 A |

*Primary Examiner*—William E. Kamm
*Attorney, Agent, or Firm*—Cushman, Darby & Cushman

[57] ABSTRACT

A method and an apparatus for measuring the variations of the foetal heart rate particularly during labor. According to this method, an average value is determined from zones where no deceleration occurs. In order to avoid variations due to small parasitic signals, this average value is compared with a filtered value, corresponding to the average value during a small number of periods of the electrocardiogram. This apparatus allows a practitioner to obtain a binary indication on the decelerations of foetal heart rate and accordingly an indication on the possible foetal stress.

17 Claims, 10 Drawing Figures

FOETAL HEART RATE APPARATUS AND METHOD IN WHICH AVERAGE FOETAL HEART RATE DURING NON-DECELERATION PERIODS IS COMPARED WITH THE AVERAGE FOETAL HEART RATE OVER A FEWER NUMBER OF PERIODS

BACKGROUND OF THE INVENTION

1. Field of the Invention

The invention relates to a method and a device for detecting and measuring the foetal heart rate (FHR) during labour and more specifically for detecting and measuring the decelerations in the heart rate during the uterine contractions during labour.

2. Description of the Prior Art

It is now known that there is a correlation between the foetal heart rate and the foetal state and accordingly the state of the child to be, as indicated in the article of G. Sturbois, M. Tournaire, A. Ripoche, R. Le Houezec, G. Breart, J. Chavine and C. Sureau published in the "Journal of Perinatal Medecine", 1-1973, PP 235-244 and entitled "Evaluation of the foetal state by automatic analysis of the heart rate".

Figure 1A:
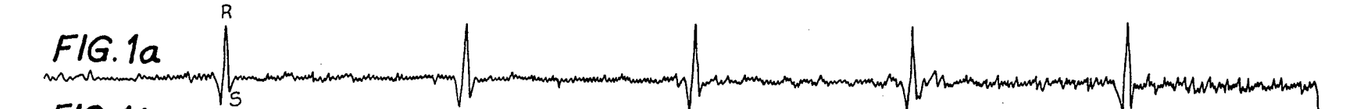
FIG. 1a shows, as an example, part of a foetal electrocardiogram
Figure 1B:
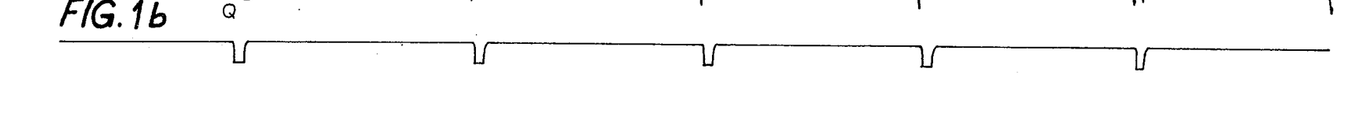
FIG. 1b shows an electronic shaped signal corresponding to this EKG.

The prior art will be explained with reference to FIG. 1a which shows as an example part of a foetal electrocardiogram (EKG). It will be appreciated that in this EKG, the QRS complex is clearly distinguishable from the background noise. This complex corresponds, with a possible phase shift, to the heart beat. As shown in FIG. 1b, the complex QRS, and more specifically the wave R, can easily be shaped by a known electronic device for providing a pulse train. The time distance between two of these pulses defines an elementary period of the EKG. And the variation of this period is in correlation with the foetal state. In an ideal case, this period is substantially regular and constant. When this period increases, that is, the time interval between two successive heart beats increases, there is a deceleration. When this time interval decreases, that is when the heart rate increases, a case of tachycardia exists. However, a direct interpretation of an EKG as shown in FIG. 1 is practically impossible. Indeed, it can be indicated, for example, that a normal FHR is of about 120 pulses/minute, i.e. the elementary period is of about 500 milliseconds. When this period increases to about 600 milliseconds, a deceleration occurs. But such an increase of the period is, in practice, not easily distinguishable from the curves shown in FIGS. 1a and 1b. However, it is necessary to be able to analysis the EKG and the possible deceleration very rapidly if one wants to help sufficiently the practitioner who must be able to make a quick decision in the event of those decelerations being repeated and reaching an "alarm threshold," decision which can be for example to intervene in the delivery of the foetus, for example by carrying out a cesarian operation or by the use of forceps.

Consequently, an electronic monitoring apparatus of the foetal heart rate (FHR) during labour which provides, from the electrical signal shown in FIG. 1b, curve, namely "period curve," the x axis of which represents the time and the y axis of which represents the time interval between a pulse and the immediately preceding pulse has been provided in the prior art. If the heart rate has a constant value, this curve is a horizontal line, but if a deceleration occurs, the y value of the curve increases. However, this period curve is complex and with difficulty interpreted by those non-specialized in the art. Moreover, this interpretation may vary from one observer to another. The use of such an apparatus by the practitioner would require special training as well as experience.

This curve is particularly difficult to interpret as it has to be considered in relationship with the changes in the intra-uterine pressure due to the contractions. Furthermore, recent studies have shown that, in the period curve, the quantitative values had to be carefully analysed. And from the period curve, three characterizing values appear as presenting clear coalitions with the foetal state. Those characteristics are: 1. the "linear" measurement of the decelerations, that is the sum of the differences between the deceleration values and the average value; 2. the total area of deceleration, that is the product of the deceleration amplitude into the deceleration duration; and 3. the simultaneous and residual deceleration surfaces, that is the deceleration surfaces measured during the contractions and the deceleration surfaces measured between the contractions, respectively. The hereabove theoretical study has been made by comparing the measurements obtained from the period curves processed by a computer, making a statistical study of a great number of cases, as it is shown in particular in the above-cited article. However, it is clear that such a processing by a computer cannot be carried out practically in each maternity center. Another important difficulty uncovered during research made with the help of a computer is that the average value of the foetal rate changes during labour, which makes it very difficult to define the deceleration threshold.

SUMMARY OF THE INVENTION

Consequently, an object of the invention is to provide a simple and compact device for determining in real time the decelerations for providing a simple and possibly binary result in order to help the practitioner make his decision during labour.

Another object of the present invention is to provide the use of the average value of N periods of the heart rate before the period being measured as the reference for determining the deceleration threshold.

A further object of the invention is to provide an electronic device and method permitting the determination of the average value.

Yet another object of the invention is to provide a device and method which will eliminate the parasitic variations of the heart rate.

To achieve these objects, the invention provides a digital electronic apparatus providing from the heart rate an average value notwithstanding the deceleration periods nor the parasitic periods, and a filtered average value of the period of some heart beats eliminating also the parasitic signals. Those values are continuously compared and the deceleration is accordingly determined and preferably integrated versus time.

Those objects, features and advantages, among others of the invention will be explained in detail in the following description.

DESCRIPTION OF THE PREFERRED EMBODIMENTS

Figure 2A:
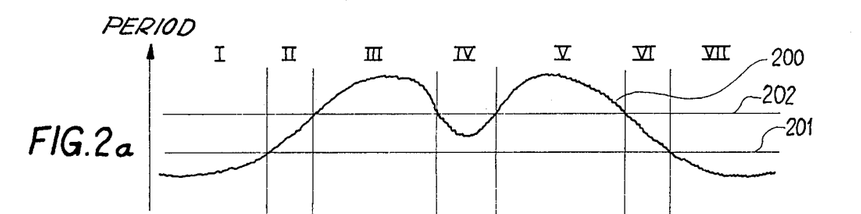
FIG. 2a shows as an example a deceleration curve and FIGS. 2b, 2c and 2d signals which can be obtained from this curve according to the invention.

FIG. 2a shows part of a heart period curve 200. The x axis represents the time and the y axis the periods. The origin of the x axis is arbitrary, but it will be emphasized that the origin of the y axis is not shown on the Figure as the variation above and below an average value are considered rather than this value itself. On the other hand, this curve 200 is smoothed. In fact, this curve is obtained from a series of points from the EKG and, generally, the deceleration duration is in the same range as the duration of a contraction. Considering a contraction of about 30 seconds and a FHR of about 120 periods/minute, one can note that the shown part of the curve 200 is obtained from about 60 points. On the other hand, usually this curve has not a great regularity, as there very often occurs artifacts, that is, spurious points.

Figure 2B:
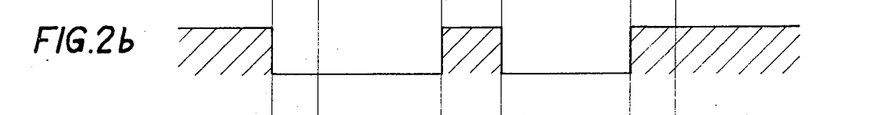
Figure 2C:
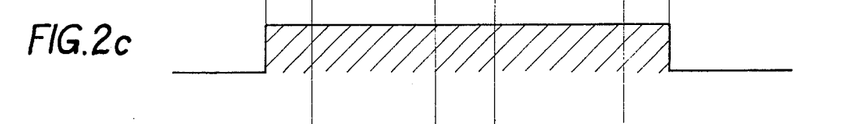

According to the invention, the average value of the period outside the deceleration periods will be determined, and the deceleration will be measured over a threshold shown by the line 201. Accordingly, referring to FIG. 2a, the deceleration will be measured in the regions II to VI, as shown in the shaded portion of the FIG. 2c. As it has been seen above, the average value of the heart rate changes, but the periods considered as deceleration periods will be eliminated from the calculation of said average value. Accordingly, as shown in FIG. 2b, the value of the period in the region I will be used for the average value calculation, then this calculation will be stopped in the regions II and III, processed again in the region IV, stopped again in the region V and processed again from the region VI onwards. Accordingly, the straight line 201 is a threshold for the deceleration calculation and for stopping the calculation of the average value while the line 202 represents a threshold for reprocessing and eventually stopping this calculation. It will be emphasized that, according to an important feature of the invention, the threshold values 201 and 202 are not predetermined constant values, but values 201 and 202 are not predetermined constant values, but values obtained from the average value by adding to this average value predetermined values which may be changed during the analysis. The "lines" 201 and 202 will accordingly, in practice, be curves which are obtained by a translation from the period average value curve as determined according to the invention and as it will be explained later on.

Figure 3:
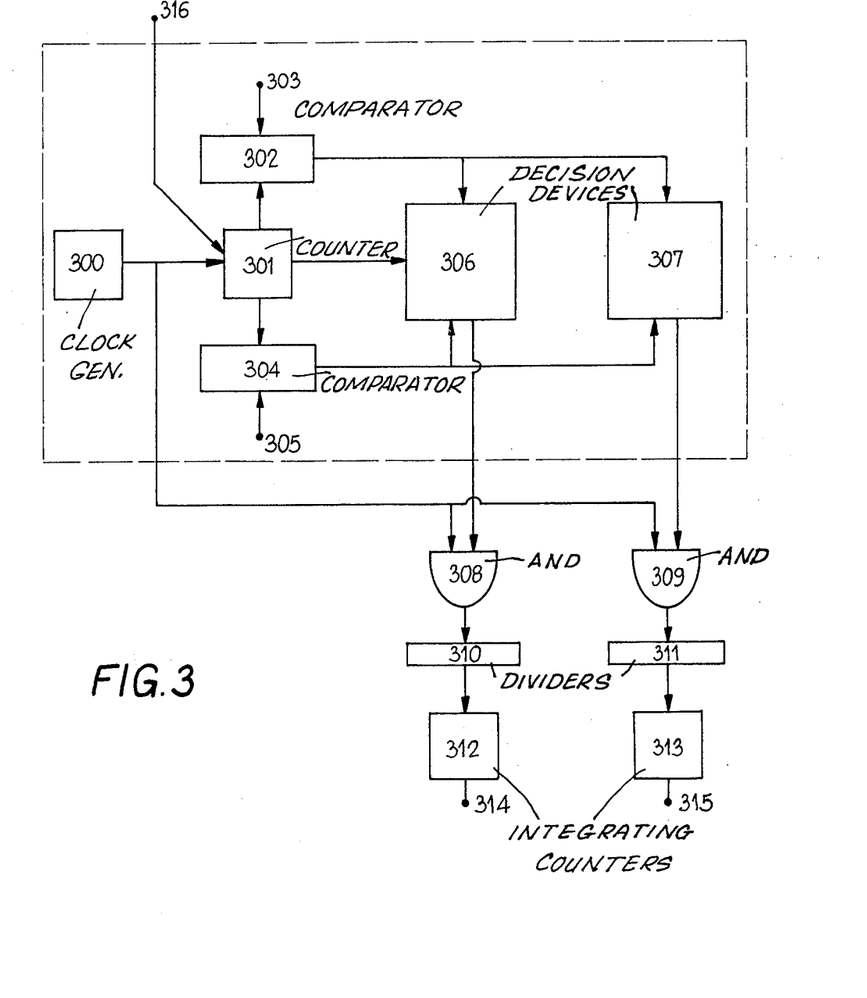
FIG. 3 is a block diagram showing a preferred embodiment of a deceleration determination device according to the invention.

Referring to FIG. 3, an embodiment of the digital device for determining the deceleration according to the invention will be disclosed. It will be appreciated that, in this FIG. 3, the filtered value and the average value are assumed to be known, the method for determining these values being explained later on in connection with FIGS. 4 and 5. In order to fully understand FIG. 3, it will be noted that the filtered value represents the value of the average period of the heart rate on some periods and without the parasitic periods, while the average value represents the average of a great number of heart cycles in the absence of deceleration periods or tachycardia, the parasitic values also being eliminated.

In FIG. 3, the numerical reference 300 shows a clock signal generator, the reference 301a counter, the references 302 and 304 comparators, the reference 303 an input terminal for the comparator 302, the reference 305 an input terminal for the comparator 304, the reference 306 a decision device for the linear deceleration calculation, the reference 307 a decision device for the deceleration area calculation, the references 308 and 309 AND gates, the references 310 and 311 dividers, the references 312 and 313 integrating counters, the references 314 and 315 output terminals and the reference 316 an input terminal of shaped EKG signals. For example, one can choose a clock signal frequency of 204,8 kHz. The counter 301 can be a counter reading up to 4,095. The divider 310 can be adapted for dividing by 1,000 and the divider 311 for dividing by 50,000. The aim of all the elements 300 to 307 is in particular to permit the obtaining, at the output of the devices 306 and 307 respectively, of a signal permitting the deceleration measurement by opening AND gates 308 and 309 which transmit, towards the counters 312 and 313, pulses from the generator 300, the number of which characterizes the deceleration.

The counter 301 is provided with a reset input connected to the terminal 316; accordingly, after receiving a pulse from the shaped EKG signal, as shown in FIG. 1b, this counter 301 is reset. Then, further to the operation of the clock signal generator 300 at 204,8 kHz, the counter 301 counts from zero to 4,095 every 20 milliseconds, until it is reset again by the following shaped EKG pulse. The comparator 302 receives on the one hand a signal representing the count of the counter 301, on the other hand a digital signal from the terminal 303, and provides a signal on one of its two outputs in accordance with the fact that the count of the counter 301 is above or below the digital value signal from the terminal 303, the terminal 303 receiving either a digital value directly representing the difference between two successive pulses of the shaped EKG, or a digital value in relationship to a filtered value of this EKG. In the same way, the comparator 304 receives on the other hand, the output signal from the counter 301, on the other hand a signal from the terminal 305 representing a digital value, said digital value being equal to the average value of the EKG period in the absence of a deceleration (or this average value plus a calculation threshold value, that is corresponding to the value represented by the curve 201 in FIG. 2a). The comparator 304 provides accordingly at its outputs, binary signals which have different states in connection with the digital value from the counter 301 above or below the digital value from the terminal 305. As it is apparent to those skilled in the art, one can easily make logic circuits 306 and 307, using the output signals of the comparators 302 and 304 providing at their outputs pulsed signals, that is providing one given logic level when the deceleration calculation has to be made and the other logic level when this calculation has not to be made. It will also be noted that the logic circuit 306, that is the decision circuit of linear deceleration calculation, is connected to an output of the counter 301. This connection inhibits the outputs of the logic circuit 306 except for the first counting cycle of the counter 301 after receiving an EKG pulse, while the decision logic circuit 307 for the calculation of the deceleration area provides an output signal for each of the counting cycles of the counter 301, that is every 20 milliseconds in the case of the above example.

The AND gates 308 and 309 are connected on the one hand with the outputs of the decision logic circuits 306 and 307 respectively, and on the other hand with the output of the clock signal generator 300. Accordingly, the AND gate 308 will authorize, for each period of the EKG signal, the passage of a pulse number, equal to the value of the deceleration for the period preceding this period or for the average of some periods preceding this period dependent on whether the terminal 303 is directly connected with the EKG period signal or with the filtered value signal of this period. This pulse number will be equal to the value of the deceleration in milliseconds. This value is divided by 1,000 by means of a divider 310 which provides an integrating counter 312 with a pulse train representing the number of seconds of linear deceleration. The AND gate 309 receives the output of the decision circuit of deceleration area calculation 307 and the output of the clock signal generator 300. Accordingly, one obtains at the output of the AND gate 309 pulses corresponding to the value in milliseconds of the deceleration period as this pulse number corresponds to the product of the linear deceleration value in milliseconds into the deceleration duration. For obtaining, at the input of the integrating counter 313, a pulse number corresponding to the value of the deceleration surface in square seconds, the invention provides for the arrangement of a divider by 50,000 311, between the output of the AND gate 309 and the input of the integrating counter 313, because each cycle of the counter 301 has a duration of 20 milliseconds in the case of the above example.

The output terminals 314 and 315 of the integrating counters 312 and 313 respectively can be connected to various display devices for indicating the variations of the deceleration, or can simply be connected to a device indicating that the deceleration values have reached a predetermined threshold. An important feature of the invention is the obtaining of such a binary indication, which is very useful for the practitioner helping a parturient woman, this practitioner being accordingly able to obtain a clear indication to assist him in his diagnosis and possibly make him intervene in order to accelerate the delivery.

It will be noted that the device disclosed in connection with FIG. 3 is only an example of an embodiment of the invention. In particular, other decision logic circuits of deceleration calculation can be provided, for example a logic circuit receiving an inhibiting signal during the contractions for indicating only the residual decelerations or, on the contrary, a logic circuit receiving an enabling signal only during the contractions for indicating only the simultaneous decelerations. On the other hand, only one of the logic circuits, such as the logic circuits 306 and 307, can be used. It will be further noted that the set comprising the counter 301 and the comparators 302 and 304 for providing indication signals to the decision logic circuits 306 and 307 is subject to various embodiments and as is known by those skilled in the art.

Figure 4:
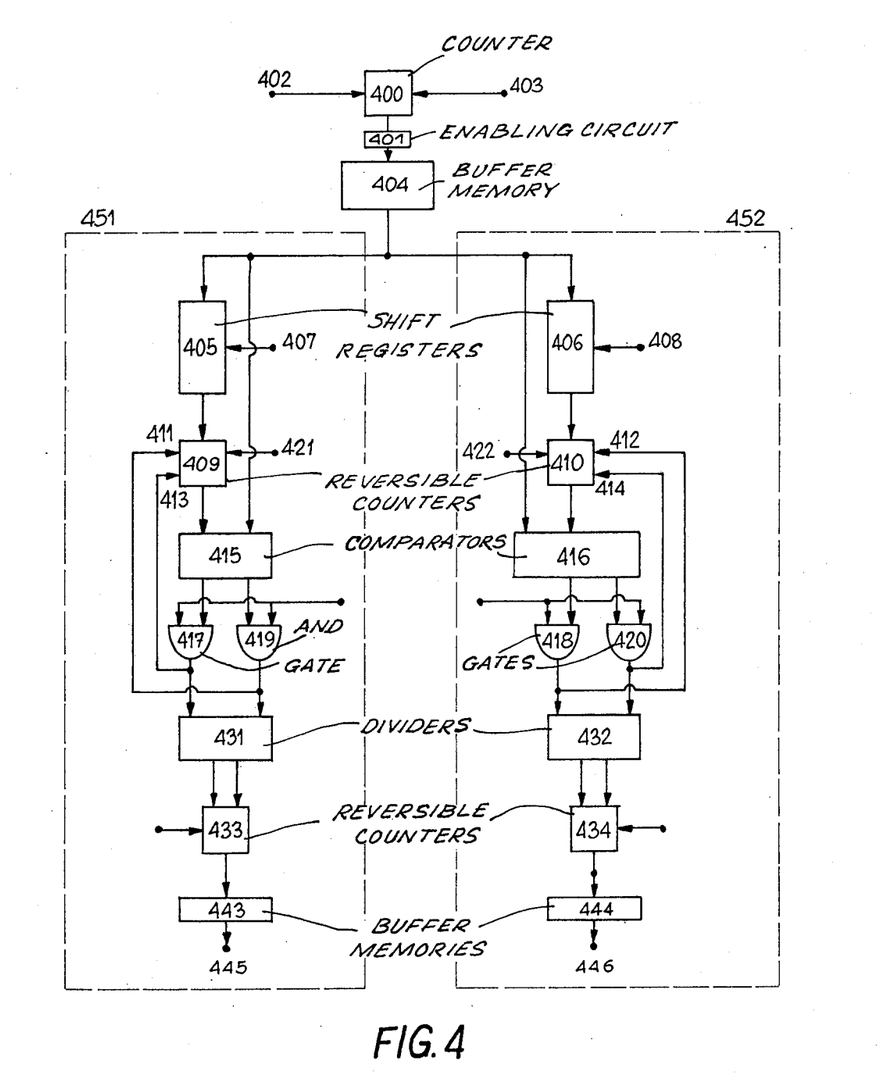
FIG. 4 is a block diagram showing a preferred embodiment of a device for determining the average value and the filtered value of the heart rate according to the invention.
Figure 5:
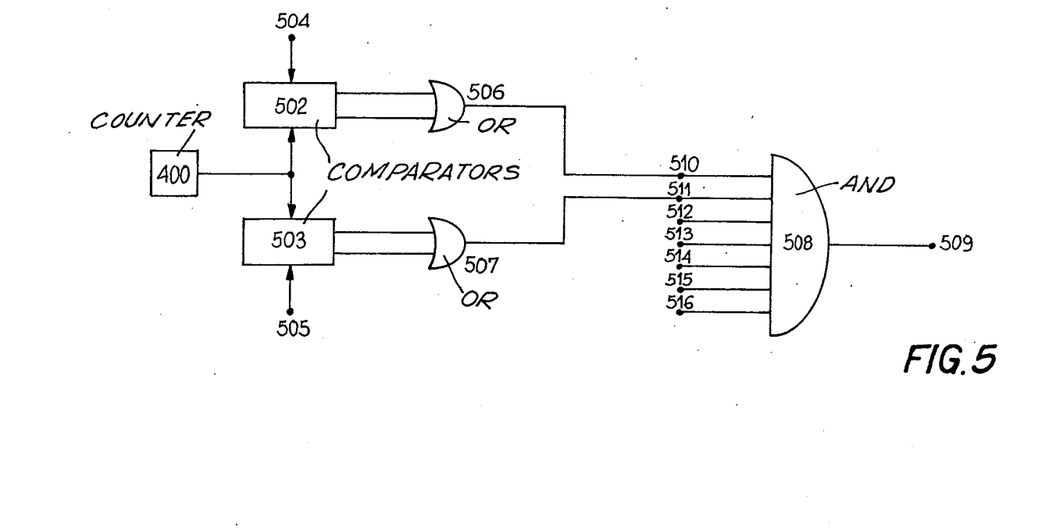
FIG. 5 is a partial block diagram of a circuit providing enabling signals from the detected period of the heart rate according to the invention.

FIG. 4 shows a preferred embodiment of a circuit for determining the average value and the filtered value for implementing a part of the process according to the invention. In this Figure, the reference 400 shows a counter in particular provided with inputs 402 and 403 ; 401 an enabling circuit ; 404 a buffer memory ; 405 and 406 shift registers ; 407 and 408 signal inputs for shifting the registers 405 and 406 respectively ; 409 and 410 reversible counters, the counter 409 being provided with a counting up input 411, a counting down input 413 and an enabling input 421, the counter 410 being provided with a counting up input 412, a counting down input 414 and an enabling input 422 ; 415 and 416 comparators ; 417, 418, 419 and 420 two-inputs AND gates ; 431 and 432 dividing circuits ; 433 and 434 reversible counters : 443 and 444 buffer memories, and 445 and 446 output terminals. The elements shown in the block 451 constitute an average value determination circuit and the elements shown in the block 452 constitute a filtered value determination circuit.

During the operation of the device shown in FIG. 4, the counter 400 is operated by a signal at the terminal 403 from a clock signal generator. In the preferred embodiment, the frequency of the generator will be of about 1kHz. The count of this counter 400 is reset and enabled again by each pulse from the EKG at its terminal 402. Immediately before each reset, the number indicated by the counter 400 is sent into a buffer memory 404 by means of a period enabling circuit 401 which will be disclosed later on in connection with FIG. 5. The output of the memory 404 is sent to a shift register having n stages 406 (this number n being small, for example 8). The shifting of the values in the stages of this shift register is carried out by a signal sent on a shifting terminal 408 of this register. Thus simply, the signal will be the shaped EKG signal whatever various enabling circuits can be provided. The output of the shift register 406 is connected with the parallel input of the counter 410 which, under the effect of the pulse applied on the terminal 422 from a validation of the heart period, assumes the value which is present in the buffer memory 404. The output of the counter 410 is sent to a first comparison input of a comparator 416, the second comparison input of which is directly connected to the output of the memory 404. The first and second inputs of the comparator 416 will accordingly receive the period value of the $(p-n)^{th}$ EKG period and the value of the pth EKG period respectively. If those values are different, the comparator will provide a signal at one of its two outputs according to the sign of this difference. The two comparator outputs are respectively connected with AND gates 418 and 420, the second input of which receives a clock signal at high frequency, for example 1MHz. The outputs of the AND gates 418 and 420 are respectively conected with counting-up and counting-down inputs 412 and 414 of the counter 410. Thus, the AND gate 418 or 420, enabled by the comparator 416, will transmit a pulse number equal to the difference between the values of the $(p-n)^{th}$ EKG period and the pth EKG period. The outputs of the AND gates 418 and 420 are also connected with the counting-up and counting-down inputs of a reversible counter 434 respectively through a n-dividing circuit 432. One accordingly obtains in the reversible counter 434, after a number of EKG periods greater than n, the average value of n periods of the EKG. This average value will be called "filtered value". It will be apparent for those skilled in the art that it is necessary for starting this calculation of the filtered value to provide the counters 400, 410 and 434 with an initial value. One will determine by means of coding wheels and of a transcoder for example, an arbitrary number used as a provisory average value for starting the operation of the device and one will obtain a filtered value which corresponds to the foetal EKG being examined after at least n periods of the EKG. The output of the reversible counter 434 is connected with an output terminal 446 through a buffer memory 444. The circuitry shown in the block 451 comprises elements which are analogous to the ones shown in the circuitry of the block 452. More specifically, the elements depicted by reference numbers which are smaller by one unity, with respect to the ones of the block 452, are analogous to the ones of this block. The main differences are the following ones : the shift register 405 is a register having N stages, N being a number which is substantially larger than the number $n$ (N can be for example 128, 256, 512, etc . . . ) and the dividing circuit 131 is a N-dividing circuit.

The circuitry shown in the block 451 provides at the output 445 and the buffer memory 443 the average value of N periods of the EKG. As in the case of the circuit 452, the counters 409 and 433 must have an initial content which is the provisory average signal, until the shifting number of the shift register 405 is equal to N.

In the above description of the circuit of FIG. 4, it has been explained that the shift registers 405 and 406 receive shifting signals from terminals 407 and 408 and that the reversible counters 409 and 410 receive enabling signals from terminals 421 and 422. In fact, those signals are present only if the preceding period complies with given validation criteria, that is a value is put in the shift registers 405 or 406 only if it complies with some given conditions As it has been stated hereabove, the memory 404 is provided with a validating input permitting it to receive or not the count of the counter 400 : a circuit providing some validations will be disclosed with reference to FIG. 5. As it can be seen in this Figure, the digital output of the counter 400 is connected with the first inputs of two comparators 502 and 503 respectively, the second inputs of those comparators being connected with terminals 504 and 505. The outputs of the comparators 502 and 503 are connected with the inputs of OR gates 506 and 507 respectively. The output of the OR gates 506 and 507 are connected with two inputs 510 and 511 of an AND gate 508 having a plurality of inputs (in FIG. 5, inputs 510 to 516 have been shown). The output 509 of the AND gate 508 provides the enabling signal for charging the memory 404. By applying at the second input 504 of the comparator 502 a digital signal representing a predetermined minimum value of the period and at the second input 505 of the comparator 503 a signal representing a predetermined maximum digital value of the period, and by connecting the outputs of the comparator 502, indicating that the signal of the first input is greater or equal to the signal of the second input, with the OR gate 506 and by applying to the OR gate 507 the output signals from the comparator 503 indicating that the signal of the first input is smaller or equal to the signal of the second input, one obtains signals at the terminals 510 and 511 at the AND gate 508 if, and only if, the value given by the counter 400 is within a predetermined range. This avoids taking into account counts of the counter 400 caused by parasitic signals of the EKG. The other terminals of the AND gate 508 will receive various enabling signals. For example, the terminal 512 can receive a signal indicating that the apparatus is ON, the terminal 513 a signal indicating that the difference between two successive values of the counter 400 is smaller than a predetermined maximum, the terminal 514 an inhibiting signal when the intra-uterine pressure reaches too large a value during the contractions, the terminal 515 an inhibiting signal operated manually, and the terminal 516 any other wanted inhibition signal.

Accordingly, one generally obtains, at the output of the memory 404, a signal which may be received by the circuit for the determination of the filtered value, but as seen hereover for the calculation of the average value, the values of the deceleration periods are also not to be taken into account, that is one wants to obtain a validating signal such as the one shown in FIG. 2b. Such a signal can be obtained by using the circuit shown in FIG. 6.

Figure 6:
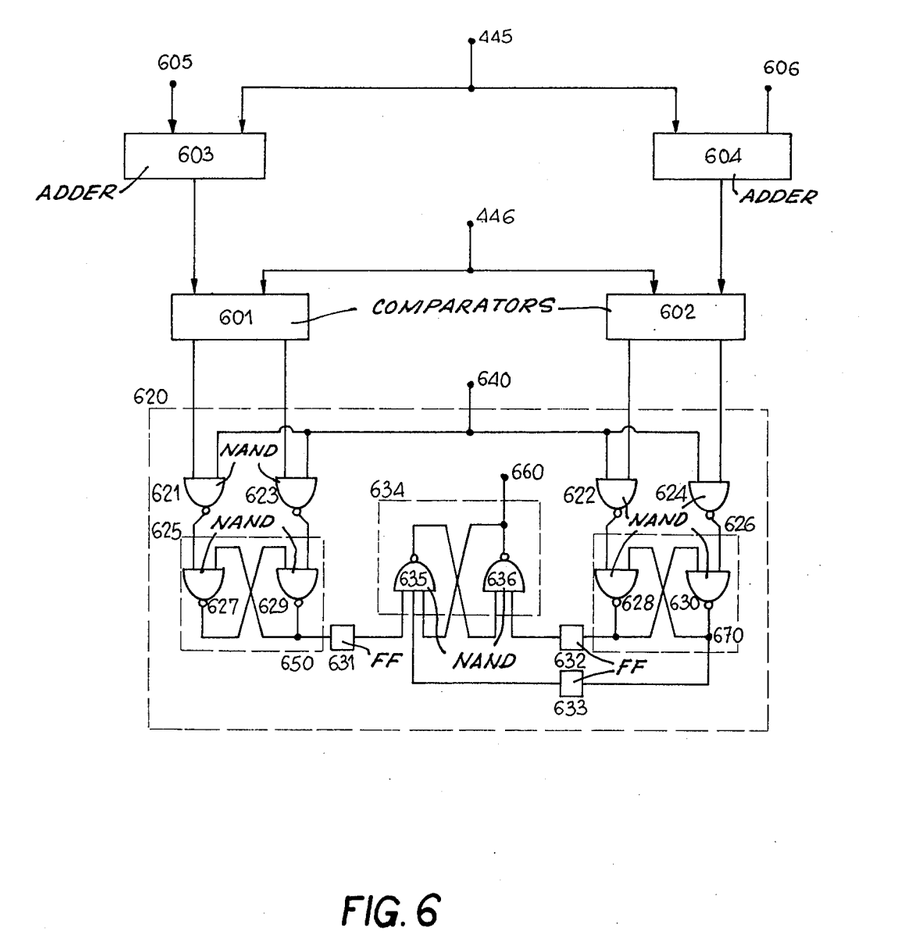
FIG. 6 is a block diagram showing a preferred embodiment of a device providing said enabling signals for a period for use in a calculation of the average value according to the invention.

Referring to FIG. 6, the references 601 and 602 indicate comparators ; the references 603 and 604 adders ; and the block 620 a logic circuit composed of NAND gates 621 to 624, and set 625 of NAND gates 627 and 629, and set 626 of NAND gates 628 and 630, and set 634 of NAND gates 635 and 636 (the gates constituting these three sets being respectively connected in order to form three flip-flop circuits) and one-shot circuits 631, 632 and 633.

Figure 2D:
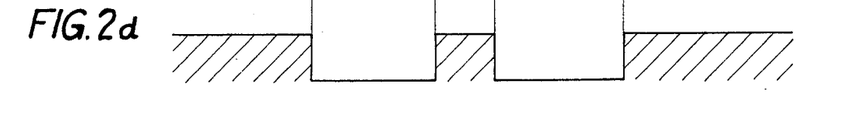

The comparators 601 and 602 receive at their first input signals from the terminal 446 (FIG. 4), that is the filtered value signals of the EKG period. The second inputs of the comparators 601 and 602 are respectively connected with the outputs of the adders 603 and 604. The first inputs of the adders 603 and 604 receive a signal from the terminal 445 (FIG. 4), that is a signal representing the digital average value of the EKG period. The second input 605 of the adder 603 receives a digital signal representing a threshold value for the deceleration calculation, as explained in connection with FIG. 2 (this value can for example be equal to 20 ms). The adder 604 receives as a second input at a terminal 606 a digital signal representing the threshold of the average value calculation, as this has also been explained in connection with FIG. 2 (this value can for example be equal to 30 ms). The superiority or inferiority outputs of the comparators 601 and 602 are connected with four first inputs of four NAND gates 621 to 624, the four second inputs of those four NAND gates receiving shaped EKG signals from a command terminal 640. The outputs of the NAND gates 621 and 623 are connected with two inputs of a flip-flop 625. One accordingly obtains at the output 650 of this flip-flop 625 the signal shown in FIG. 2c corresponding to the threshold 201 of FIG. 2a. The outputs of the NAND gates 622 and 624 are connected with the two inputs of the flip-flop 626 and one obtains at the output 670 of this flip-flop the signal shown in FIG. 2d, corresponding to the threshold 202 of FIG. 2a. The circuitry comprising the oneshot circuits 631, 632 and 633 and the flip-flop circuit 634 permits to obtain at the output 660 of this flip-flop the signal shown in FIG. 2b, which is the useful signal for enabling or inhibiting the input of a value for the calculation of the average value in the shift register 405 of the average value calculation circuit disclosed in connection with FIG. 4.

It will be noted that for the sake of simplicity, the circuits of the FIGS. 3 and 6 have been independently disclosed. It will however appear to those skilled in the art that some of the elements of those two circuits are common as one obtains, at the output 650 shown in FIG. 6, the signal shown in FIG. 2c which is usable in the decision logic circuit for the deceleration calculation.

Moreover, in the preferred embodiment disclosed hereinabove, the EKG electrical signal has been used as the heart rate signal. However, the heart rate can be provided by various other known means, for example from audio-frequency or ultra-audio-frequency obtained by means of a microphone arranged on the abdomen of the future mother.

This invention is not limited to the described embodiments but variants and modifications, which are apparent to the man skilled in the art, may be applied thereto.

What is claimed is:

1. A method for quantitatively determining the decelerations of a foetal heart rate, comprising the following steps:
   sensing the foetal heart rate and providing an electric heart rate signal;
   forming from the heart rate signal a heart period signal comprising a plurality of heart beats;
   forming from the heart period signal a signal corresponding to a filtered average value of the heart period over a given number of heartbeats;
   inhibiting in the heart period signal the values corresponding to the deceleration periods;
   forming, from the non-inhibited value, an average signal of a number of heart periods greater than said given number;
   comparing the instantaneous values of the filtered value and of the average value;
   integrating the difference signal between said average value and said filtered value in the case where the filtered value is greater than the average value.

2. A method according to claim 1 further comprising the step of comparing the integrated value with a determined threshold value which can be time varying in order to provide an alarm signal.

3. A method according to claim 1 wherein, during the step of forming the heart period signal, various enabling steps are provided to avoid the elaboration of this period signal from parasitic signals, said enabling steps comprising in particular a validation of the minimum, a validation of the maximum, and a validation of the maximum of the difference, between two successive periods.

4. A method according to claim 1 wherein, during the step of forming an average value signal, the values of the heart period are not taken into account for the calculation of the average value when they become larger than the value of the average value prior calculated plus a predetermined first value called threshold value of the deceleration calculation.

5. A method according to claim 4 wherein the values of the heart period are again taken into account when they become smaller than the value of the prior calculated average value plus a second predetermined value larger than the first predetermined value called threshold of the average value calculation and wherein the values of the heart period are no longer taken into account when they become larger than this second threshold without having reached a value smaller than the first threshold.

6. A method according to claim 1 wherein during the step of forming a filtered value signal, only one period is taken into account in the determination of the filtered value, whereby the heart period signal is directly compared with the average value signal during the comparison step.

7. A method according to claim 1 wherein, during the comparison step, the filtered value is compared with the average value plus the threshold value of the deceleration calculation.

8. A method according to claim 1 wherein, during the integration step, the integration is made once for each heart period, whereby one obtains an indication of the linear deceleration in time units.

9. A method according to claim 1 wherein, during the integrating step, the integration is made several times at regular time intervals during each heart period whereby one obtains an indication so-called deceleration area in square time units.

10. A method according to claim 1 wherein the integration is inhibited during or after the uterine pressure is above a predetermined threshold, whereby one obtains an indication of the residual or simultaneous deceleration respectively.

11. Apparatus for quantitatively determining the decelerations of a foetal heart rate comprising :
   a sensing means for providing an electric heart signal from the foetal heart rate ;
   a digital means for providing from the heart signal a digital heart period signal ;
   a digital means for providing from the heart period signal a digital filtered value of the heart signal ;
   a digital means for forming from the heart period signal a digital average value signal of a great number of heart periods ;
   an inhibiting means for not taking into account, in the formation of the heart period signal, the values corresponding to the deceleration period ;
   a comparison means for comparing the instantaneous value of said filtered value and of said average value ;
   an integrating means for adding the difference signal between said average value and said filtered value when the filtered value is larger than the average value (deceleration steps).

12. Apparatus according to claim 11 wherein the determination of the digital filtered value is made from an enabled digital heart period signal by means of a serial circuit comprising a n-stages shift register (406), a reversible counter (410), a comparator (416), two parallel AND gates (418) and (420), a n-divider (432), a reversible counter (434) ; the second input of the comparator (416) receiving directly the period signal ; the up and down counting inputs of the reversible counter (410) being connected with the outputs of the AND gates (418) and (420) respectively.

13. Apparatus according to claim 12 wherein the number n is comprised between 1 and 16 .

14. Apparatus according to claim 11 wherein the determination of the filtered value is made by a serial circuit comprising a N-stages shift register (405), a reversible counter (409), a comparator (415), two parallel connected AND gates (417) and (419), a N-divider (431), a reversible counter (433) ; the second input of the comparator (415) receiving the filtered period signal ; the up and down counting inputs of the reversible counter (409) being connected with the outputs of AND gates (417) and (419) respectively.

15. Apparatus according to claim 14 wherein the number N is chosen greater than 100.

16. An apparatus as in claim 14 wherein said inhibiting means includes enabling circuits for stopping calculation of the average value whenever the values of the foetal heart period are larger than a first threshold value and resuming calculation of the average value whenever thereafter the values of the foetal heart period are smaller than a second threshold value, said second threshold value being greater than the calculated average value.

17. An apparatus as in claim 14, wherein said inhibiting means includes enabling circuits for stopping calculation of the average value and wherein said given number is 1.